United States Patent [19]

Hein

[11] 4,081,332
[45] Mar. 28, 1978

[54] EXTRACTIVE DISTILLATION OF $C_5$ HYDROCARBONS USING ACETONITRILE AND ADDITIVES

[75] Inventor: Richard William Hein, Hudson, Ohio

[73] Assignee: The B. F. Goodrich Company, Akron, Ohio

[21] Appl. No.: 718,368

[22] Filed: Aug. 27, 1976

[51] Int. Cl.$^2$ .......................... B01D 3/40; C07C 7/08
[52] U.S. Cl. ...................................... 203/51; 203/53; 203/56; 203/60; 203/63; 203/64; 252/364; 260/677 A; 260/681.5 R
[58] Field of Search ...................... 203/51, 56, 60, 57, 203/58, 64, 53, 63; 260/681.5 R, 677 A; 252/364

[56] References Cited

U.S. PATENT DOCUMENTS

| | | | |
|---|---|---|---|
| 3,436,438 | 4/1969 | Takao et al. | 203/60 |
| 3,510,405 | 5/1970 | Takao et al. | 203/60 |
| 3,515,762 | 6/1970 | Koide et al. | 203/60 |
| 3,681,202 | 8/1972 | Funkhouser | 203/60 |
| 3,707,575 | 12/1972 | Muller et al. | 203/60 |
| 3,775,259 | 11/1973 | Sarno | 203/60 |
| 3,803,258 | 4/1974 | Weitz et al. | 203/51 |
| 3,898,135 | 8/1975 | Tidwell et al. | 203/60 |

Primary Examiner—Wilbur L. Bascomb, Jr.
Attorney, Agent, or Firm—Joe A. Powell; J. Hughes Powell, Jr.

[57] ABSTRACT

In the extractive distillation of $C_5$ hydrocarbons with different degrees of unsaturated using acetonitrile, an increase in the selectivity of acetonitrile is obtained when also using with acetonitrile small amounts of at least one compound selected from the group consisting of dimethylformamide, dimethylsulfoxide, morpholine, furfural, N-methylpyrrolidone, 3-methoxypropionitrile, gamma-butyrolactone, ethylene glycol monomethyl ether, diethylene glycol monomethyl ether, ethylene glycol monoethyl ether, and diethylene glycol monoethyl ether.

12 Claims, 1 Drawing Figure

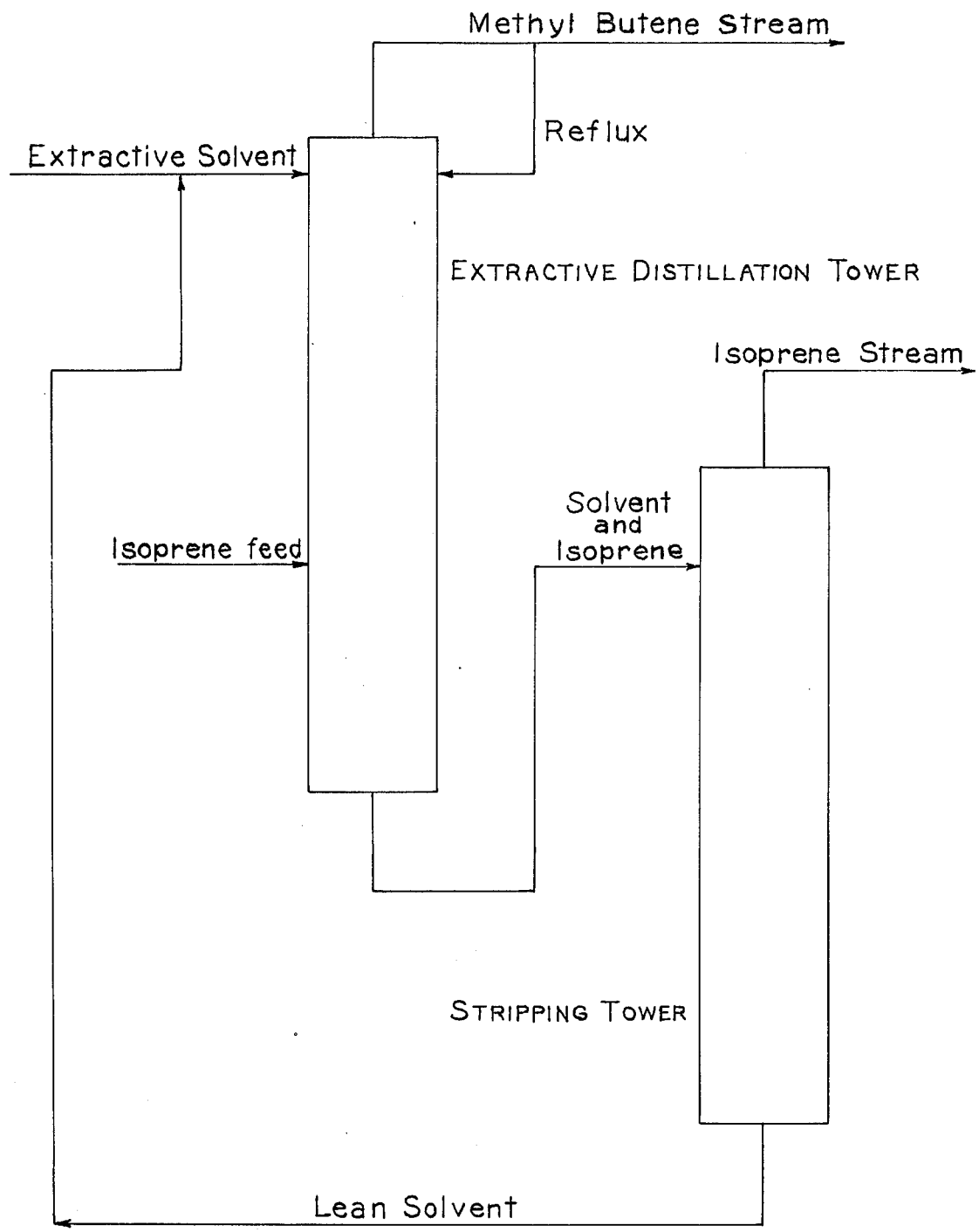

EXTRACTIVE DISTILLATION OF C₅ HYDROCARBONS USING ACETONITRILE AND ADDITIVES

BACKGROUND OF THE INVENTION

Certain hydrocarbon mixtures are difficult to separate by ordinary distillation, therefore, extractive distillation may be used to effect such separation. Extractive distillation is extensively used to separate hydrocarbons with like numbers of carbon atoms but with different degrees of unsaturation. Extractive distillation involves distilling the mixture to be separated in the presence of a relatively higher boiling solvent which is selective for at least one component of the mixture. An extractive distillation process is normally performed by introducing the selective solvent into a distillation column at a point near the top of the distillation column and allowing the solvent to flow down the distillation column as the distillation proceeds. As the hydrocarbon vapors travel up the distillation column, they are contacted by the solvent and the more highly unsaturated hydrocarbons are caused to have a reduced relative vapor pressure compared to the other unsaturated hydrocarbons. The bottoms of the distillation column then consists primarily of the solvent plus the more highly unsaturated hydrocarbon. The more highly unsaturated hydrocarbon may be removed from the solvent in a stripping column or by other suitable means and the lean solvent is recycled to the extractive distillation column.

Extractive distillation is especially useful in separating mixtures of $C_4$ or $C_5$ hydrocarbons with different degrees of unsaturation. The $C_4$ and $C_5$ hydrocarbons are normally obtained from catalytic or thermal cracking, dehydrogenation, including oxidative dehydrogenation, or Fisher-Tropsch reactions and the like. Isoprene is a particularly desirable $C_5$ hydrocarbon.

The $C_5$ feed stock used in the production of isoprene contains isoprene and 2-methyl-2-butene along with other hydrocarbons. In the production of isoprene, it is necessary to separate isoprene from 2-methyl-2-butene. Since isoprene is the more unsaturated of the two $C_5$ hydrocarbons, an extractive distillation solvent is employed which will selectively extract the isoprene vapors and collect in the bottoms while allowing the 2-methyl-2-butene vapors to pass upward and be withdrawn from the top of the extractive distillation column. Isoprene and the solvent is withdrawn from the bottom and passed to a stripper where the isoprene is separated from the fat solvent and the lean solvent is then returned to the distillation column.

In the extractive distillation process of separating isoprene from 2-methyl-2-butene, several solvents are proposed in the art, including furfural, acetonitrile, dimethylformamide, N-methylpyrrolidone. Small amounts of water are normally used with these solvents. Water is not a cosolvent but serves to improve the selectivity of the solvent and to lower the temperature in the stripping process.

Unfortunately, many of the solvents proposed in the art are either relatively poor in selectively, corrosive, or result in equipment fouling.

U.S. Pat. No. 3,898,135 discloses an extractive distillation solvent comprising a mixture of 3-methoxypropionitrile with small amounts of water and furfural. This solvent mixture improves the separation process of $C_4$ hydrocarbons by reducing fouling in the distillation equipment.

U.S. Pat. No. 3,890,208 discloses an extractive distillation cosolvent comprising a mixture of furfural with small amounts of water an an acyclic ketone. This cosolvent has improved selectivity in separating n-butane and butene-1 as compared to a solvent of furfural and water.

Acetonitrile with small amounts of water has been found to be a prticularly desirable extractive distillation solvent in the separation of isoprene from 2-methyl-2-butene because of its lack of corrosion and fouling of the equipment and also because of the cost and availability of acetonitrile. U.S. Pat. No. 3,230,157 discloses a process for producing high purity isoprene wherein acetonitrile with up to 5 weight percent of water is used as the extractive distillation solvent.

However, it is desirable to improve the efficiency of an extractive distillation process employing acetonitrile as the solvent for separating isoprene from 2-methyl-2-butene.

SUMMARY OF THE INVENTION

In the extractive distillation of $C_5$ hydrocarbons wth different degrees of unsaturation using acetonitrile, an increase in the selectivity of acetonitrile is obtained when also using with acetonitrile small amounts of at least one compound selected from the group consisting of dimethylformamide, dimethylsulfoxide, morpholine, furfural, N-methylpyrrolidone, 3-methoxypropionitrile, gamma-butyrolactone, ethylene glycol monomethyl ether, diethylene glycol monomethyl ether, ethylene glycol monoethyl ether, and diethylene glycol monoethyl ether. Water can be present in the solvent or it can be non-aqueous. The solvents are especially useful in the separation of isoprene from 2-methyl-2-butene.

BRIEF DESCRIPTION OF THE DRAWING

The attached schematic drawing containing word labels is a flow sheet illustrating the process of the invention.

DETAILED DESCRIPTION

In the extractive distillation process of separating $C_5$ hydrocarbons with different degrees of unsaturation, the selectivity of acetonitrile extractive distillation solvent is improved by adding to the acetonitrile certain novel additives.

To the acetonitrile extractive distillation solvent is added from about 2 to about 50 parts by weight per 100 parts by weight of acetonitrile of at least one additive selected from the group consisting of dimethylformamide, dimethylsulfoxide, morpholine, furfural, N-methylpyrrolidone, 3-methoxypropionitrile, gamma-butyrolactone, ethylene glycol monomethyl ether, diethylene glycol monomethyl ether, ethylene glycol monoethyl ether, and diethylene glycol monethyl ether. Preferably, the additive is present at levels of from about 2 to about 20 parts by weight per 100 parts by weight of acetonitrile. One or more than one additive may be added to the acetonitrile. Water can be present in the acetonitrile in levels of up to about 30 parts by weight of water per 100 parts by weight of acetonitrile or the acetonitrile can be non-aqueous. Preferably, water is present at levels of from about 2 to about 10 parts by weight per 100 parts by weight of acetonitrile.

Although the selectivity of acetonitrile is further improved by the presence of some of the additives in quantities greater than 20 parts by weight of additive per 100 parts by weight of acetonitrile, for an extractive distillation process now using acetonitrile as a solvent, it is preferred to add only small amounts of from about 2 to about 20 parts by weight of additive per 100 parts by weight of acetonitrile so as not to require changes in the process equipment design.

The additive can be added to the acetonitrile by charging the desired amount of the additive to the acetonitrile make-up tank or surge tank. The combination of acetonitrile and additive becomes the extractive distillation solvent.

The additive must have a boiling point greater than the boiling point of acetonitrile which is about 82° C. If the boiling point of the additive was lower than the boiling point of acetonitrile, then some of the additive would be taken off with the isoprene during the stripping process.

The present extractive distillation process for separating $C_5$ hydrocarbons is conducted in any type of extractive distillation equipment known to those skilled in the art to be useful in the extractive distillation of $C_5$ hydrocarbons. The equipment may include baffle columns, bubble trays, packed columns, and the like. The length and diameter of the column will depend on the flow rates required and the degree of extraction required.

The process is carried out by introducing the $C_5$ hydrocarbons to be separated into the extractive distillation column at a point below the mid-point of the column. An extractive distillation solvent of acetonitrile and at least one of the polar additives is introduced into the column at a point above the entry point of the $C_5$ hydrocarbon feed mixture. Preferably, the extractive distillation solvent is introduced into the column at a point at or above the top one-third of the column. Temperature and pressure conditions are maintained such that the hydrocarbon feed is in vapor phase and the solvent is in liquid phase. The vapor phase contacts the liquid phase and the more unsaturated $C_5$ hydrocarbon is extracted into the liquid phase. An overhead is taken off that contains a predominant amount of the more saturated $C_5$ hydrocarbons. The fat solvent with the more unsaturated $C_5$ hydrocarbons are taken off the bottom. The bottoms stream is taken to a stripper where the solvent is separated from the more unsaturated $C_5$ hydrocarbon by ordinary distillation and the lean solvent is recycled to the extractive distillation column. There can be various arrangements of refluxes for part of the overhead, premixing of refluxes into solvent and reboilers for the bottom.

The quantity of solvent required will vary depending on the efficiency of the separation required and the type of equipment used. The quantity of solvent may range from about 1 to about 20 parts by weight of solvent per 1 part by weight of $C_5$ feed mixture. Preferably, the quantity of solvent is from about 3 to about 10 parts by weight of solvent per 1 part by weight of $C_5$ feed mixture.

The reflux ratio in which the column is operated will vary according to the solvent to feed ratio, the composition of the feed mixture, the degree of separation desired, and the theoretical plate efficiency of the column. The reflux ratio can be from about 0.1 to 1 to about 20 to 1. Preferably, the reflux ratio is from about 1 to 1 to about 5 to 1.

The temperature of the extractive distillation process will vary according to hydrocarbon mixture that is being separated and the pressure being used. The temperature is from about 50° to about 350° F. Preferably, the temperature is from about 175° to about 275° F. The extractive distillation process can be carried out at atmospheric pressure, subatmospheric pressure or superatmospheric pressure. Pressures of up to about 200 psig can be used. Preferably, the pressure is from about 10 psig to about 50 psig.

The selectivity of an extractive distillation solvent for separating isoprene from 2-methyl-2-butene is evaluated by measuring the relative volatilities of a mixture of isoprene and 2-methyl-2-butene in the presence of the solvent. Relative volatility is obtained by the following equation:

Relative volatility = $(A/B)/(C/D)$ wherein $A$ is the mole percent of 2-methyl-2-butene in the vapor phase, $B$ is the mole percent of 2-methyl-2-butene in the liquid phase, $C$ is the mole percent of isoprene in the vapor phase, and $D$ is the mole percent of isoprene in the liquid phase. The higher the relative volatility the easier the isoprene and 2-methyl-2-butene are to separate. Differences in relative volatility of only 0.01 are significant in an extractive distillation operation.

In order to further illustrate the present invention, the following examples are presented.

EXAMPLE 1

This example is submitted to show the increase in the relative volatility of a $C_5$ hydrocarbon feed mixture of 2-methyl-2-butene and isoprene when the additives are present in non-aqueous acetonitrile solvent. An Othmer still is used to arrive at the relative volatility data. To the Othmer still is added a mixture of 2-methyl-2-butene and isoprene along with the solvent. The solvent to hydrocarbon feed ratio is 85 parts by weight of solvent per 15 parts by weight of the 2-methyl-2-butene and isoprene hydrocarbon feed mixture. The contents of the still is boiled and the vapors are condensed and returned to the still as a liquid. The still is allowed to come to an equilibrium for about 3 hours. Samples of the liquid in the still and the condensed vapors are taken simultaneously and analyzed by Chromatographic area. From the analysis of the two samples, the relative volatility is calculated. The relative volatility results of non-aqueous acetonitrile solvent with the additives is compared with non-aqueous acetonitrile solvent without the additives in Table I. Table I shows that the relative volatility of the $C_5$ hydrocarbon feed is increased when the additive dimethylformamide, dimethylsulfoxide, morpholine, 3-methoxypropionitrile, ethylene glycol monomethyl ether, or diethylene glycol monomethyl ether is present in non-aqueous acetonitrile as compared to the relative volatility with only non-aqueous acetonitrile as the solvent. When the additive morpholine, 3-methoxypropionitrile, ethylene glycol monomethyl ether, or diethylene glycol monomethyl ether is added to the non-aqueous acetonitrile the relative volatility is higher than when either non-aqueous acetonitrile or the additive is used as the sole solvent. Surprisingly a number of known $C_5$ hydrocarbon solvents, namely 4-methylmorpholine, tetrahydrofuran, trimethyl phosphite, and Bis-2-methoxyethyl ether when added to the non-aqueous acetonitrile doen not increase the relative volatility of the $C_5$ hydrocarbon feed mixture.

TABLE 1
ADDITIVES TO NON-AQUEOUS ACETONITRILE

| Run | Solvent - Wt. % | Equilibrium Temp. °C | 2-Methyl-2-butene/Isoprene Relative Volatility |
|---|---|---|---|
| 1. | 100 - Acetonitrile | 57.0 | 1.450 |
| 2. | 95 - Acetonitrile<br>5 - Dimethyl Formamide | 57.5 | 1.476 |
| 3. | 90 - Acetonitrile<br>10 - Dimethyl Formamide | 57.5 | 1.476 |
| 4. | 85 - Acetonitrile<br>15 - Dimethylformamide | 59.0 | 1.481 |
| 5. | 75 - Acetonitrile<br>25 - Dimethylformamide | 60.0 | 1.472 |
| 6. | 75 - Acetonitrile<br>25 - Dimethylsulfoxide | 58.5 | 1.482 |
| 7. | 95 - Acetonitrile<br>5 - Morpholine | 57.0 | 1.445 |
| 8. | 85 - Acetonitrile<br>15 - Morpholine | 57.5 | 1.486 |
| 9. | 75 - Acetonitrile<br>25 - Morpholine | 58.5 | 1.434 |
| 10. | 50 - Acetonitrile<br>50 - Morpholine | 60.5 | 1.461 |
| 11. | 100 - Morpholine | 79.0 | 1.344 |
| 12. | 90 - Acetonitrile<br>10 - 3-Methoxypropionitrile | 57.0 | 1.485 |
| 13. | 85 - Acetonitrile<br>15 - 3-Methoxypropionitrile | 57.5 | 1.511 |
| 14. | 75 - Acetonitrile<br>25 - 3-Methoxypropionitrile | 57.5 | 1.508 |
| 15. | 50 - Acetonitrile<br>50 - 3-Methoxypropionitrile | 57.5 | 1.444 |
| 16. | 100 - 3-Methoxypropionitrile | 58.5 | 1.475 |
| 17. | 95 - Acetonitrile<br>5 - Ethylene glycol monomethyl ether | 57.5 | 1.506 |
| 18. | 85 - Acetonitrile<br>15 - Ethylene glycol monomethyl ether | 58.0 | 1.471 |
| 19. | 75 - Acetonitrile<br>25 - Ethylene glycol monomethyl ether | 58.0 | 1.479 |
| 20. | 100 - Ethylene glycol monomethyl ether | 67.0 | 1.394 |
| 21. | 95 - Acetonitrile<br>5 - Diethylene glycol monomethyl ether | 58.0 | 1.520 |
| 22. | 90 - Acetonitrile<br>10 - Diethylene glycol monomethyl ether | 58.0 | 1.520 |
| 23. | 85 - Acetonitrile<br>15 - Diethylene glycol monomethyl ether | 58.0 | 1.499 |
| 24. | 75 - Acetonitrile<br>25 - Diethylene glycol monomethyl ether | 58.0 | 1.467 |
| 25. | 50 - Acetonitrile<br>50 - Diethylene glycol monomethyl ether | 58.0 | 1.468 |
| 26. | 100 - Diethylene glycol monomethyl ether | 74.0 | 1.344 |
| 27. | 95 - Acetonitrile<br>5 - 4-Methyl morpholine | 57.5 | 1.405 |
| 28. | 90 - Acetonitrile<br>10 - 4-Methyl morpholine | 57.5 | 1.388 |
| 29. | 75 - Acetonitrile<br>25 - 4-Methyl morpholine | 59.5 | 1.374 |
| 30. | 90 - Acetonitrile<br>10 - Tetrahydrofuran | 57.0 | 1.439 |
| 31. | 85 - Acetonitrile<br>15 - Tetrahydrofuran | 57.0 | 1.391 |
| 32. | 90 - Acetonitrile<br>10 - Trimethyl phosphite | 57.5 | 1.421 |
| 33. | 85 - Acetonitrile<br>15 - Trimethyl phosphite | 57.5 | 1.434 |
| 34. | 90 - Acetonitrile<br>10 - Bis-2-methoxyethyl ether | 56.5 | 1.448 |
| 35. | 85 - Acetonitrile<br>15 - Bis-2-methoxyethyl ether | 58.0 | 1.449 |
| 36. | 75 - Acetonitrile<br>25 - Bis-2-methoxyethyl ether | 58.0 | 1.392 |

EXAMPLE II

The preceding example is repeated to show the increase in the relative volatility of a mixture of 2-methyl-2-butene and isoprene when the additive is present in a 98% aqueous acetonitrile solvent (98% acetonitrile, 2% water). The same procedure and conditions for arriving at relative volatility is used in this example as is used in example 1. Table II shows the relative volatility of the $C_5$ hydrocarbon feed with a solvent of 98% aqueous acetonitrile as compared with 98% aqueous acetonitrile with the additive. Table II shows that when small amounts of the additive dimethylformamide, furfural, N-methylpyrrolidone, 3-methoxypropionitrile, or ethylene glycol monomethyl ether are added to the 98% aqueous acetonitrile, the relative volatility of the $C_5$ hydrocarbon mixture is higher than when 98% aqueous acetonitrile is used alone as the solvent.

TABLE II
ADDITIVES TO 98% ACETONITRILE - 2% WATER (98% AQUEOUS ACETONITRILE)

| Run | Solvent Wt. % | Equilibrium Temp. °C | 2-Methyl-2-butene/isoprene Relative Volatility |
|---|---|---|---|
| 37. | 100 - 98% Aqueous acetonitrile | 54.0 | 1.453 |
| 38. | 95 - 98% Aqueous acetonitrile<br>5 - Dimethyl formamide | 54.5 | 1.495 |
| 39. | 90 - 98% Aqueous acetonitrile<br>10 - Dimethyl formamide | 56.5 | 1.487 |
| 40. | 85 - 98% Aqueous acetonitrile<br>15 - Dimethyl formamide | 57.0 | 1.485 |
| 41. | 95 - 98% Aqueous acetonitrile<br>5 - Furfural | 53.0 | 1.469 |
| 42. | 90 - 98% Aqueous acetonitrile<br>10 - Furfural | 53.0 | 1.494 |
| 43. | 85 - 98% Aqueous acetonitrile<br>15 - Furfural | 53.5 | 1.467 |
| 44. | 75 - 98% Aqueous acetonitrile<br>25 - Furfural | 55.0 | 1.436 |
| 45. | 95 - 98% Aqueous acetonitrile<br>5 - N-methylpyrrolidone | 54.4 | 1.474 |
| 46. | 90 - 98% Aqueous acetonitrile<br>10 - N-methylpyrrolidone | 53.0 | 1.483 |
| 47. | 85 - 98% Aqueous acetonitrile<br>15 - N-methylpyrrolidone | 54.5 | 1.488 |
| 48. | 75 - 98% Aqueous acetonitrile<br>25 - N-methylpyrrolidone | 56.0 | 1.484 |
| 49. | 95 - 98% Aqueous acetonitrile<br>5 - 3-methoxypropionitrile | 53.0 | 1.499 |
| 50. | 90 - 98% Aqueous acetonitrile<br>10 - 3-methoxypropionitrile | 53.0 | 1.504 |
| 51. | 85 - 98% Aqueous acetonitrile<br>15 - 3-methoxypropionitrile | 54.0 | 1.499 |
| 52. | 75 - 98% Aqueous acetonitrile<br>25 - 3-methoxypropionitrile | 54.5 | 1.484 |
| 53. | 95 - 98% Aqueous acetonitrile<br>5 - Ethylene glycol monomethyl ether | 51.5 | 1.462 |
| 54. | 90 - 98% Aqueous acetonitrile<br>10 - Ethylene glycol monomethyl ether | 53.0 | 1.434 |

EXAMPLE III

The preceding examples are repeated to show the increase in the relative volatility of a mixture of 2-methyl-2-butene and isoprene when the additive is present in a 93% aqueous acetonitrile (93% acetonitrile, 7% water). The same procedure and conditions for arriving at relative volatility is used in these examples as is used in examples 1 and 2. Table III shows the relative volatility of the $C_5$ hydrocarbon feed with a solvent of 93% aqueous acetonitrile as compared with 93% aqueous acetonitrile with the additive. Table III shows that when small amounts of the additive dimethylformamide, dimethylsulfoxide, morpholine, N-methylpyrrolidone, 3-methoxypropionitrile, gamma-butyrolactone, ethylene glycol monomethyl ether, diethylene glycol monomethyl ether, ethylene glycol monethyl ether, or diethylene glycol monoethyl ether are added to the 93% aqueous acetonitrile, the relative volatility of the $C_5$ hydrocarbon is higher than when 93% aqueous acetonitrile is used alone as the solvent, surprisingly sulfolane, a known C₅ hydrocarbon solvent, does not increase the relative volatility when used as an additive to 93% aqueous acetonitrile.

TABLE III

ADDIVITES TO 93% ACETONITRILE - 7% WATER
(93% AQUEOUS ACETONITRILE)

| Run | Solvent Wt. % | Equilibrium Temp. °C | 2-Methyl-2-butene/ isoprene Relative Volatility |
|---|---|---|---|
| 55. | 100 - 93% Aqueous acetonitrile | 51.0 | 1.458 |
| 56. | 95 - 93% Aqueous acetonitrile<br>5 - Dimethylformamide | 52.0 | 1.491 |
| 57. | 90 - 93% Aqueous acetonitrile<br>10 - Dimethylformamide | 52.0 | 1.476 |
| 58. | 85 - 93% Aqueous acetonitrile<br>15 - Dimethylformamide | 52.0 | 1.473 |
| 59. | 95 - 93% Aqueous acetonitrile<br>5 - Dimethylsulfoxide | 46.0 | 1.503 |
| 60. | 90 - 93% Aqueous acetonitrile<br>10 - Dimethylsulfoxide | 46.0 | 1.498 |
| 61. | 85 - 93% Aqueous acetonitrile<br>15 - Dimethylsulfoxide | 46.0 | 1.505 |
| 62. | 80 - 93% Aqueous acetonitrile<br>20 - Dimethylsulfoxide | 46.0 | 1.486 |
| 63. | 75 - 93% Aqueous acetonitrile<br>25 - Dimethylsulfoxide | 46.0 | 1.480 |
| 64. | 95 - 93% Aqueous acetonitrile<br>5 - Morpholine | 47.0 | 1.472 |
| 65. | 90 - 93% Aqueous acetonitrile<br>10 - Morpholine | 47.0 | 1.484 |
| 66. | 85 - 93% Aqueous acetonitrile<br>15 - Morpholine | 47.0 | 1.512 |
| 67. | 80 - 93% Aqueous acetonitrile<br>20 - Morpholine | 49.0 | 1.480 |
| 68. | 75 - 93% Aqueous acetonitrile<br>25 - Morpholine | 49.0 | 1.461 |
| 69. | 95 - 93% Aqueous acetonitrile<br>5 - N-methylpyrrolidone | 51.0 | 1.478 |
| 70. | 90 - 93% Aqueous acetonitrile<br>10 - N-methylpyrrolidone | 51.5 | 1.461 |
| 71. | 85 - 93% Aqueous acetonitrile<br>15 - N-methylpyrrolidone | 52.0 | 1.483 |
| 72. | 75 - 93% Aqueous acetonitrile<br>25 - N-methylpyrrolidone | 54.5 | 1.536 |
| 73. | 95 - 93% Aqueous acetonitrile<br>5 - 3-methoxypropionitrile | 51.5 | 1.503 |
| 74. | 90 - 93% Aqueous acetonitrile<br>10 - 3-methoxypropionitrile | 51.5 | 1.508 |
| 75. | 85 - 93% Aqueous acetonitrile<br>15 - 3-methoxypropionitrile | 51.5 | 1.499 |
| 76. | 75 - 93% Aqueous acetonitrile<br>25 - 3-methoxypropionitrile | 51.5 | 1.489 |
| 77. | 85 - 93% Aqueous acetonitrile<br>15 - Gamma-butyrolactone | 48.5 | 1.464 |
| 78. | 80 - 93% Aqueous Acetonitrile<br>20 - Gamma-butyrolactone | 49.0 | 1.480 |
| 79. | 75 - 93% Aqueous acetonitrile<br>25 - Gamma-butyrolactone | 48.5 | 1.470 |
| 80. | 50 - 93% Aqueous acetonitrile<br>50 - Gamma-butyrolactone | 48.5 | 1.410 |
| 81. | 95 - 93% Aqueous acetonitrile<br>5 - Ethylene glycol monomethyl ether | 53.0 | 1.478 |
| 82. | 90 - 93% Aqueous acetonitrile<br>10 - Ethylene glycol monomethyl ether | 53.0 | 1.488 |
| 83. | 85 - 93% Aqueous acetonitrile<br>15 - Ethylene glycol monomethyl ether | 53.5 | 1.447 |
| 84. | 75 - 93% Aqueous acetonitrile<br>25 - Ethylene glycol monomethyl ether | 54.0 | 1.449 |
| 85. | 95 - 93% Aqeous acetonitrile<br>5 - Diethylene glycol monomethyl ether | 48.0 | 1.470 |
| 86. | 85 - 93% Aqueous acetonitrile<br>15 - Diethylene glycol monomethyl ether | 48.0 | 1.458 |
| 87. | 80 - 93% Aqueous acetonitrile<br>20 - Diethylene glycol monomethyl ether | 48.0 | 1.432 |
| 88. | 95 - 93% Aqueous acetonitrile<br>5 - Ethylene glycol monoethyl ether | 52.0 | 1.501 |
| 89. | 90 - 93% Aqueous acetonitrile<br>10 - Ethylene glycol monoethyl ether | 52.0 | 1.478 |
| 90. | 85 - 93% Aqueous acetonitrile<br>15 - Ethylene glycol monoethyl ether | 52.0 | 1.458 |
| 91. | 75 - 93% Aqueous acetonitrile<br>25 - Ethylene glycol monoethyl ether | 53.0 | 1.449 |
| 92. | 95 - 93% Aqueous acetonitrile<br>5 - Diethylene glycol monoethyl ether | 47.0 | 1.501 |
| 93. | 90 - 93% Aqueous acetonitrile<br>10 - Diethylene glycol monoethyl ether | 47.0 | 1.507 |
| 94. | 85 - 93% Aqueous acetonitrile<br>15 - Diethylene glycol monoethyl ether | 47.0 | 1.467 |
| 95. | 80 - 93% Aqueous acetonitrile<br>20 - Diethylene glycol monoethyl ether | 47.0 | 1.482 |
| 96. | 75 - 93% Aqueous acetonitrile<br>25 - Diethylene glycol monoethyl ether | 47.5 | 1.451 |
| 97. | 95 - 93% Aqueous acetonitrile<br>5 - Sulfolane | 47.0 | 1.431 |
| 98. | 85 - 85-93% Aqueous acetonitrile<br>15 - Sulfolane | 47.0 | 1.433 |

EXAMPLE IV

An extractive distillation tower with sixty theoretical stages may be used to separate a mixture of hydrocarbons containing isoprene, 2-methyl-2-butene, pentene-1, isopentane, 2-methyl-1-butene, n-pentane, t-pentene-2, t-piperylene, and cyclopentene. The hydrocarbon feed is introduced into the extractive distillation tower at a point below the midpoint of the tower and the extractive distillation solvent containing 90 weight percent 98% aqueous acetonitrile (2% water) and 10 weight percent N-methylpyrrolidone is introduced to the extractive distillation tower at a point above the midpoint of the tower. This extractive solvent has a 2-methyl-2-butene/isoprene relative volatility of 1.483. The hydrocarbon feed is introduced at a temperature of 164° F and the extractive distillation solvent is introduced at a temperature of 136° F. The top of the extractive distillation tower is maintained at a temperature of 125° F and a pressure of 26 psia. The bottom of the extractive distillation tower is maintained at a temperature of 214° F and a pressure of 45 psia. A stream is taken from the top of the extractive distillation tower which is lean in isoprene. From the overhead stream a reflux stream is returned to the extractive distillation tower. The reflux stream is at a temperature of 110° F. The extractive distillation solvent rich in isoprene is taken from the bottom of the extractive distillation tower and passed to a stripper, where the isoprene is separated by distillation from the fat extractive distillation solvent and the lean solvent is then recycled to the extractive distillation tower. The top of the stripper tower is maintained at a temperature of 125° F and a pressure of 26 psia. The bottom of the stripper tower is maintained at a temperature of 222° F and a pressure of 33 psia. As compared to extractive distillation with 98% aqueous acetonitrile (2% water) alone, which has a 2-methyl-2-butene/isoprene relative volatility of 1.453, with this mixture a calculated isoprene purity increase from 68.2 mole percent to 74.9 mole percent may be obtained with less 2-methyl-2-butene impurity from 25.4 mole percent to 20.8 mole percent remaining in the isoprene at a decreased reflux ratio. This mixture of isoprene and 2- methyl-2-butene, along with other impurities, may be passed to a final fractionation tower where they are further separated to give an isoprene purity in excess of 99 mole percent. This high purity isoprene is suitable for polymerization.

Isoprene monomer is readily polymerized to make polyisoprene. Polyisoprene is a synthetic rubber used in the manufacture of tires, conveyor belts and sponge products. Isoprene is also copolymerized with isobutylene to make butyl rubber which is used in the manufacture of tires and inner tubes.

I claim:

1. In an extractive distillation process for separating mixtures of $C_5$ hydrocarbons with different degrees of unsaturation including the steps of introducing a selective solvent to an extractive distillation column, introducing said hydrocarbon mixtures to be extractively distilled at a point below the point of introduction of said selective solvent, selectively extracting the more unsaturated hydrocarbon to form a liquid solvent fraction rich in the more unsaturated hydrocarbon, withdrawing a vaporous hydrocarbon fraction rich in the less unsaturated hydrocarbon as overhead from the top of said extractive distillation column, withdrawing the solvent rich in the more unsaturated hydrocarbon from the bottom of said extractive distillation column, passing the rich solvent with the more unsaturated hydrocarbon to a stripping column where the solvent and the more unsaturated hydrocarbon are separated, and recycling the lean solvent to said extractive distillation column, the improvement comprising employing as said selective solvent from about 67 to about 98 weight percent acetonitrile and from about 2 to about 33 weight percent of at least one additive selected from the group consisting of dimethylformamide, 3-methoxypropionitrile, ethylene glycol monomethyl ether, diethylene glycol monomethyl ether, ethylene glycol monoethyl ether and diethylene glycol monoethyl ether, said weight percents being based on dry solvent.

2. An extractive distillation process of claim 1 wherein the $C_5$ hydrocarbons contain 2-methyl-2-butene and isoprene.

3. An extractive distillation process of claim 2 containing up to about 20 weight percent water.

4. An extractive distillation process of claim 3 containing up to about 7 weight percent water.

5. An extractive distillation process of claim 4 wherein the additive is present in amounts of from about 5 to about 15 weight percent.

6. An extractive distillation process of claim 5 wherein the additive is selected from the group consisting of dimethylformamide, ethylene glycol monomethyl ether and diethylene glycol monomethyl ether.

7. An extractive distillation process of claim 6 wherein the weight ratio of solvent to $C_5$ hydrocarbon is from about 1 to 1 to about 20 to 1.

8. An extractive distillation process of claim 7 wherein the weight ratio of solvent to $C_5$ hydrocarbon is from about 3 to 1 to about 10 to 1.

9. An extractive distillation solvent for separating mixtures of $C_5$ hydrocarbons with different degrees of unsaturation comprising from about 67 to about 98 weight percent acetonitrile and from about 2 to about 33 weight percent of at least one additive selected from the group consisting of dimethylformamide, 3-methoxypropionitrile, ethylene glycol monomethyl ether, diethylene glycol monomethyl ether, ethylene glycol monoethyl ether and diethylene glycol monoethyl ether, said weight percents being based on dry solvent.

10. An extractive distillation solvent of claim 9 containing up to about 20 weight percent water.

11. An extractive distillation solvent of claim 10 wherein the additive is present in amounts of from about 5 to about 15 weight percent.

12. An extractive distillation solvent of claim 11 wherein the additive is selected from the group consisting of dimethylformamide, ethylene glycol monomethyl ether and diethylene glycol monomethyl ether.

* * * * *